United States Patent [19]

Carlos

[11] 4,192,812

[45] Mar. 11, 1980

[54] OXIDATION OF WAXES IN THE PRESENCE OF LONG CHAIN QUATERNARY AMMONIUM AND PHOSPHONIUM COMPOUNDS

[75] Inventor: Donald D. Carlos, Grayson, Ky.

[73] Assignee: Ashland Oil, Inc., Ashland, Ky.

[21] Appl. No.: 918,131

[22] Filed: Jun. 22, 1978

[51] Int. Cl.$^2$ .......................... C09F 7/02; C11C 3/00
[52] U.S. Cl. .................................. 260/406; 260/451; 208/3; 252/426; 252/429 R
[58] Field of Search ................ 260/451, 406; 208/3

[56] References Cited

U.S. PATENT DOCUMENTS

| | | | |
|---|---|---|---|
| 2,338,634 | 1/1944 | Fuchs | 260/451 |
| 2,674,613 | 4/1954 | Nelson | 208/3 X |
| 2,704,294 | 3/1955 | Morgan | 260/451 |
| 3,054,814 | 9/1962 | Jason | 260/406 |
| 3,803,137 | 4/1974 | Egan | 260/585 B |

*Primary Examiner*—John F. Niebling
*Attorney, Agent, or Firm*—Van D. Harrison, Jr.

[57] ABSTRACT

The oxidation of hydrocarbon waxes to corresponding fatty acids through the use of conventional catalysts and oxidizing gases such as air is promoted by the addition of quaternary ammonium and phosphonium salts to the catalyst-wax mixture.

7 Claims, No Drawings

OXIDATION OF WAXES IN THE PRESENCE OF LONG CHAIN QUATERNARY AMMONIUM AND PHOSPHONIUM COMPOUNDS

NATURE OF THE INVENTION

This invention relates to the oxidation of hydrocarbon waxes. More particularly, it is concerned with a process for oxidizing hydrocarbon waxes to produce useful oxygenated wax products such as higher molecular weight fatty acids.

PRIOR ART

Oxidized petroleum fractions including oxidized petroleum waxes have, in the past, been employed as the source of saponifiable material in the production of lubricating greases and in forumlation of protective coatings. The oxidates employed for these purposes have been obtained by oxidizing selected petroleum fractions under controlled conditions such that the oxidation proceeds only to a limited extent.

A number of catalysts have been used to promote the oxidation of paraffinic hydrocarbons. U.S. Pat. No. 1,788,799 discloses calcium or aluminum oxide and compounds of manganese to be useful catalysts in the oxidation of paraffin wax with air mixed with nitric oxides. Potassium permanganate is shown to be a popular catalyst in U.S. Pat. Nos. 2,818,419; 2,847,439; 2,894,970 and 3,050,455. U.S. Pat. No. 2,808,423 discloses the use of manganese salts of carboxylic acids in conjunction with magnesium or calcium salts of carboxylic acids. U.S. Pat. No. 2,895,978 discloses the use of the hydroxide of calcium, barium, strontium zinc or magnesium as an oxidation catalyst. U.S. Pat. No. 2,674,613 shows the use of sodium carbonate, manganese palmitate and other manganese salts as accelerators in the air oxidation of hydrocarbons with potassium permanganate or ammonium vanadate.

The oxidation of paraffinic hydrocarbons by agitating them with air at elevated temperatures has associated therewith certain difficulties. Some petroleum fractions are not easily oxidized by prior art processes and eventhough oxidizable, in some instances, require a prolonged period of agitation with air before the rate of oxidation becomes sufficient so that the reaction can proceed to completion. Another problem sometimes associated with wax oxidation is the discoloration of the final wax oxidate product obtained.

OBJECT OF THE INVENTION

One object of this invention is to provide an improved process for the oxidation of petroleum paraffinic hydrocarbons. Another object of the invention is to provide a process for oxidizing hydrocarbon fractions more easily than has heretofore been possible.

SUMMARY OF THE INVENTION

Briefly stated, this invention comprises a process for oxidizing hydrocarbon paraffins comprising blowing an oxidizing gas through said paraffin mixture to which has been added a conventional oxidizing catalyst and a promoting amount of a quaternary salt. The quaternary salt has the formula:

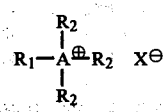

where $R_1$ is an aliphatic hydrocarbon radical of 12 or more carbon atoms, $R_2$ is an aliphatic hydrocarbon radical of 1–12 carbon atoms, A is nitrogen or phosphorus and $X^\ominus$ is chloride, bromide, iodide, sulfate or bisulfate. Throughout the remainder of this description, the term quaternary salt is intended to include both quaternary ammonium and quaternary phosphonium salts.

The oxidation is conducted under suitable conditions of gas-flow and temperature to oxidize the hydrocarbon fraction to a desired acid number.

In another aspect, this invention comprises a catalyst for oxidizing saturated paraffinic hydrocarbons to their corresponding fatty acids comprising a mixture of a quaternary salt compound and an oxidizing agent.

DESCRIPTION OF THE INVENTION

Although a number of quaternary compounds are deemed suitable for the promoter catalyst in the process of this invention, preferred promoters are dodecyltrimethylammonium chloride or a mixture of quaternary compounds having the formula:

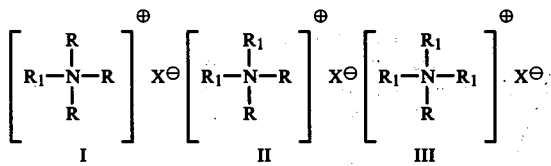

wherein R collectively represents the alkyl residue of a primary alcohol mixture composed of 30–70 wt. percent of (a) straight-chain $C_{16}$–$C_{22}$ alcohols and correspondingly from 70–30 wt. percent of (b) $C_8$–$C_{15}$ Oxo alcohols consisting essentially of a mixture of straight-chain and single methyl branced isomers, said (a) and (b) being in relative proportions so that from about 95–80 wt. percent of said $R_1$ groups are straight-chain alkyl and correspondingly from 5–20 wt. percent are said branched alkyl, R is a $C_1$–$C_3$ alkyl group, X represents a chloride, bromide or iodide anion, and wherein said mixture of quaternaries is essentially composed of 0–10 wt. percent of compounds of Formula I, 60–85 wt. percent of compounds of Formula II, and 5–25 wt. percent of compounds of Formula III, said mixture being prepared by ammonolysis of a mixture of the corresponding $R_1OH$ alcohols and subsequent quaternization of the ammonolysis product.

The preparation and composition of these quaternary compounds is disclosed in U.S. Pat. No. 3,803,137 which is hereby incorporated by reference.

The hydrocarbons useful in this process are the conventional feedstocks previously used as oxidizer feedstock. Ordinarily, said feedstock comprises a mixture of saturated hydrocarbons having an average number of carbon atoms per molecule of 20 to 100. A particular characteristic of some feedstocks is the high concentration of nitrogen present in the molecular structure of some of the hydrocarbons making up the feedstock. The presence of nitorgen appears to inhibit the oxidation of the hydrocarbons to their corresponding acids when blown with air in the presence of the presently used catalysts such as potassium premanganate or other manganese catalysts. However, the addition of quaternary compounds appears to overcome the inhibition of oxidation and serves to initiate the oxidation of the hydrocarbon.

The oxidizing catalysts used in conjunction with the quaternary compounds include the presently available permanganate salts of sodium and potassium, oxides, hydroxides and fatty acid salts of sodium, potassium and calcium, and carbonates of sodium and potassium.

Preferably, at least one hydrocarbon component in the quaternary compound has a carbon chain of at least 10 carbon atoms. The quaternary compound is added to the hydrocarbon fraction in a concentration of between 0.5 and 2 parts by weight per 100 parts of hydrocarbon. Ordinarily, the process will be carried out as a batch process. Air or another oxidizing gas is forced through the reaction mixture at a rate of between 0.5 and 10 liters per liter of hydrocarbon per minute at a temperature of between 150° and 180° C. Ordinarily, the temperature will rise as the oxidation proceeds so that only minimal heat may be required for the oxidation. The oxidation process is conducted at a pressure of between 50 and 400 psig (4.4–28.2 atmospheres). The process is discontinued when a desired acid number is reached. The term "acid number" is defined to mean the number of milligrams of potassium hydroxide required to neutralize 1 gram of sample.

EXAMPLE I

A number of air oxidations were conducted in laboratory tests using a 1 liter Parr bomb. In each test, the reactor charge amounted to approximately 500 cc of hydrocarbon. To the hydrocarbon material was added the weight of the catalyst as shown in the accompanying table. The feedstocks studied included both slack waxes and petrolatum samples. The reaction conditions were approximately three hours for each reaction at a temperature of approximately 320° F. (160° C.), a pressure of 200 psig, (14.6 atmospheres) and an air input rate of 2.8 liters (measured at 25° C. and 1 atmosphere) per liter of reaction charge per minute. Acid number determinations were made at the end of each three-hour run. The results are shown in the attached table.

TABLE I

| Run No. | Reaction Mixture Composition, Parts By weight | | Acid No. of Oxidate | Comments |
| --- | --- | --- | --- | --- |
| 1 | Ca(OH)$_2$ | 1 | | No oxidation after three hours |
| | Feedstock | 99 | 0.2 | |
| 2 | Ca(OH)$_2$ | 1 | | Brief induction period |
| | Quaternary(1) | 1 | | |
| | Feedstock | 98 | 39.5 | |
| 3 | Na$_2$CO$_3$ | 1 | | Brief induction period |
| | Feedstock | 99 | 20.2 | |
| 4 | Na$_2$CO$_3$ | 2 | | Induction period of three hours |
| | Feedstock | 98 | 21.6 | |
| 5 | Na$_2$CO$_3$ | 1 | | No induction period required |
| | Quaternary | 1 | | |
| | Feedstock | 98 | 19.3 | |

(1)Quaternary compound was a quaternary compound prepared according to U.S. Pat. No. 3,803,137 and marketed by Ashland Chemical Company under the tradename ADOGEN A-432.

From the foregoing Table it is readily apparent that in runs 1, 3 and 4, in the absence of the added quaternary compound, oxidation of the oxidizer feedstock was slow or did not occur at all. In runs 2 and 5, the addition of the quaternary compound readily promoted the oxidation of the oxidizer feedstock.

I claim:

1. A process for oxidizing a liquid mixture of saturated paraffinic hydrocarbons having an average of about 20 to about 100 carbon atoms per molecule to a desired acid number comprising blowing an oxidizing gas through said liquid mixture in the presence of an oxidizing catalyst and a promoting amount of a quaternary salt having the formula:

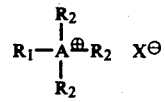

where $R_1$ is an aliphatic hydrocarbon radical of 12 or more carbon atoms, $R_2$ is an aliphatic hydrocarbon radical of 1–12 carbon atoms, A is nitrogen or phosphorus and $X^\ominus$ is chloride, bromide, iodide, sulfate or bisulfate.

2. A process for oxidizing liquid hydrocarbon fractions to a desired acid number comprising blowing an oxidizing gas through said liquid hydrocarbon in the presence of an oxidizing catalyst and a promoting amount of dodecyltrimethylammonium chloride.

3. A process for oxidizing liquid hydrocarbon fractions to a desired acid number comprising blowing an oxidizing gas through said liquid hydrocarbon in the presence of an oxidizing catalyst and a promoting amount of a mixture of quaternary ammonium compounds having the formula:

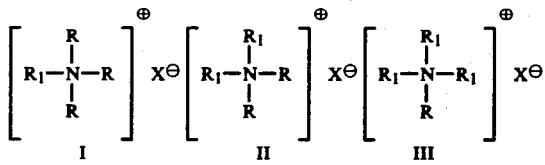

wherein R collectively represents the alkyl residue of a primary alcohol mixture composed of 30–70 wt. percent of (a) straight-chain $C_{16}$–$C_{22}$ alcohols and correspondingly from 70–30 wt. percent of (b) $C_8$–$C_{15}$ Oxo alcohols consisting essentially of a mixture of straight-chain and single methyl branched isomers, said (a) and (b) being in relative proportions so that from about 95–80 wt. percent of said $R_1$ groups are straight-chain alkyl and correspondingly from 5–20 wt. percent are said branched alkyl, R is a $C_1$–$C_3$ alkyl group, X represents a chloride, bromide or iodide anion, and wherein said mixture of quaternaries is essentially composed of 0–10 wt. percent of compounds of Formula I, 60–85 wt. percent of compounds of Formula II, and 5–25 wt. percent of compounds of Formula III, said mixture being prepared by ammonolysis of a mixture of the corresponding $R_1OH$ alcohols and subsequent quaternization of the ammonolysis product.

4. The process of claim 1 wherein the rate of oxidizing gas blowing is between about 0.5 and about 10 liters (measured at 25° C. and 1 atmosphere) per liter of liquid hydrocarbon.

5. The process of claim 1 wherein the concentration of quaternary compound is between about 0.05 and about 2 parts per 100 parts of liquid hydrocarbon.

6. The process of claim 1 wherein the concentration of oxidizing catalyst is between about 0.05 and about 2 parts per 100 parts of liquid hydrocarbon.

7. The process of claim 1 wherein the oxidizing catalyst is selected from the group consisting of permanganate salts, oxides and hydroxides of sodium, potassium and calcium, and carbonates of sodium and potassium.

* * * * *